United States Patent
Ernster

Patent Number: 5,968,042
Date of Patent: Oct. 19, 1999

[54] MONOPOLAR SUCTION COAGULATOR

[76] Inventor: Joel A. Ernster, 715 N. Cascade Ave., Colorado Springs, Colo. 80903

[21] Appl. No.: 08/877,436

[22] Filed: Jun. 17, 1997

[51] Int. Cl.⁶ .................................................. A61B 17/39
[52] U.S. Cl. ................................ 606/49; 604/21; 606/41
[58] Field of Search ........................... 606/41, 42, 45–52; 604/21, 22, 35; 600/374

[56] References Cited

U.S. PATENT DOCUMENTS

| | | |
|---|---|---|
| 3,974,833 | 8/1976 | Durden, III . |
| 4,269,174 | 5/1981 | Adair ......................................... 606/49 |
| 4,931,407 | 6/1990 | Broadwin et al. . |
| 4,932,952 | 6/1990 | Wojciechowicz ........................... 606/49 |
| 4,960,419 | 10/1990 | Rosenberg . |
| 5,085,657 | 2/1992 | Ben-Simhon . |
| 5,102,410 | 4/1992 | Dressel . |
| 5,267,994 | 12/1993 | Gentelia et al. . |
| 5,277,696 | 1/1994 | Hagen ........................................ 606/49 |
| 5,322,503 | 6/1994 | Desai ........................................ 604/21 |
| 5,334,183 | 8/1994 | Wuchinich . |
| 5,335,671 | 8/1994 | Clemnet . |
| 5,364,395 | 11/1994 | West, Jr. . |
| 5,417,697 | 5/1995 | Wilk et al. . |
| 5,423,830 | 6/1995 | Schneebaum et al. . |
| 5,451,223 | 9/1995 | Ben-Simhon . |
| 5,522,815 | 6/1996 | Durgin, Jr. et al. ....................... 606/50 |
| 5,571,101 | 11/1996 | Ellman et al. ............................. 606/45 |
| 5,730,742 | 3/1998 | Wojciechowicz ........................... 606/49 |

*Primary Examiner*—Michael Peffley
*Attorney, Agent, or Firm*—Gibson, Dunn & Crutcher LLP

[57] ABSTRACT

An electrosurgical coagulator (10) has a hollow elongate tube (20), insulation material (30) covering a major portion of the tube (20), a handle (40) of molding material covering a proximal section of the tube (20) and insulation material (30), a power cord (50) electrically connected to the tube (20), and a contact pin (52) terminating the power cord (50) for attachment to an external power supply (60). The tube (20), insulation (30), and handle (40) are coaxial; the handle (40) extends furthest proximally and terminates in a fitting (42) that is engageable with an external suction source (70). The tube (20) has a distal portion (22) for contacting to bleeding tissue and coagulating the same, the distal portion being beveled and having a notch (25) for superior resolution and ease of positioning, clog prevention, and ease of cleaning.

8 Claims, 1 Drawing Sheet

MONOPOLAR SUCTION COAGULATOR

FIELD OF THE INVENTION

The present invention relates to the field of electrosurgical devices, and more particularly to a monopolar cauterizing coagulator for nasal hemostasis having a tip shaped for excellent angulation and a notch allowing simultaneous suctioning and removal of blood and smoke while cauterizing.

BACKGROUND OF THE INVENTION

Electrosurgical devices for coagulating bleeding tissue have been available for some time. Most generally, such devices include a hollow conductive tube having an insulating coating over all but a most distal tube portion, so that the distal tube portion forms a generally annular ablating electrode; a hollow insulating handle coaxially surrounding the tube; a suction source attached to a proximal portion of the tube for evacuating excess blood and smoke from the surgical site; and wire electrical connectors attached to a power source for electrically activating the electrode. Such a device is described in, for example, U.S. Pat. No. 4,932,952 (Wojciechowicz, Jr., 1990).

Hemostasis in the nose can be desirable to treat a severe nosebleed, and to close surgically created wounds in the nose. None of the electrosurgical coagulation devices known to the inventor have been engineered with the particular problems associated with nasal hemostasis. While known electrosurgical devices are used to effect nasal hemostasis, such devices have not been optimized. In particular, the electrodes do not provide for precision coagulation. The generally ring-shaped electrodes have a circular cross section and therefore do not allow for selective ablation except by repositioning the entire device—stated another way, the circular electrodes are blunt and do not provide highly selective control. While electrosurgical knives are known (see for example U.S. Pat. No. 4,960,419 (Rosenberg, 1990), attaching a separate blade to a suction tube increases the manufacturing complexity as compared to the above described method of electrically activating a conductive tube so that the tube is both an electrode and a suction element. Other shaped electrosurgical tips are disclosed in U.S. Pat. No. 5,267,994—again, such tips are physically distinct from a suction tube and are therefore more complex and may be less reliable than the simpler cylindrical device first described above. A tip having more precision than the cylindrical shape, while maintaining its essential simplicity and reliability, will provide an improved coagulation device.

Electrosurgical suction coagulators can clog with blood or tissue during operation, interrupting the hemostasis procedure and requiring additional effort by the operating physician and staff. A venting port in the handle of a device may reduce clogging, but does not prevent it. See Wojciechowicz, Jr. for a description of such ports. Ventilation ports also hinder 360 degree operation of a device, in that a physician cannot easily rotate a device while maintaining a finger over the port.

A coagulator that is more postionalble, more accessible to a tangential passage, less prone to clogging, and easier to clean if clogged than known coagulators is therefore a welcome advance in the art, particularly when such benefits are realized in a rugged, reliable, and relatively simple design.

SUMMARY OF THE INVENTION

The present invention is an electrosurgical suction coagulator. The coagulator has a hollow elongate tube, insulation material covering a major portion of the tube, a handle of molding material covering a proximal section of the tube and insulation material, a power cord electrically connected to the tube, and a contact pin terminating the power cord for attachment to a power supply. The tube, insulation, and handle are coaxial; the handle extends furthest proximally and terminates in a fitting that is engageable with an external suction source.

The tube has a distal portion for contacting to bleeding tissue and coagulating the same, the distal portion being beveled and having a notch formed therein. The bevel and notch provide a "pointed" coagulating surface, which can be more selectively positioned than a conventional tube, thereby allowing greater coagulation resolution. The notch in the tip allows for ventilation in the tube, which reduces the incidence of clogging and facilitates cleaning and unclogging the tube when necessary. The coagulator tube of the present invention is preferably of somewhat smaller diameter than known coagulator tubes, allowing for easier manipulation within a nostril.

KEY TO REFERENCE NUMERALS

Figure 1:
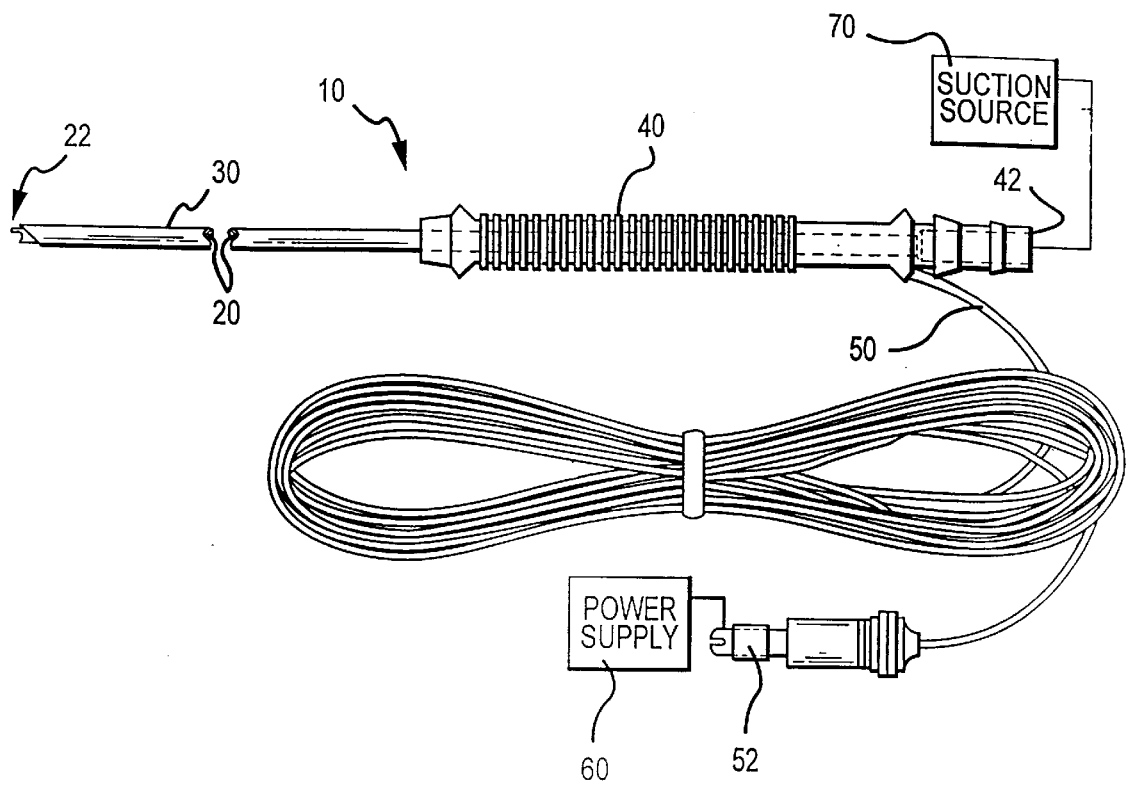
FIG. 1 is a side elevation view of a coagulator according to the present invention.

10 coagulator
22 distal portion of tube
23a distal face section
25 notch
40 handle
50 power cord
70 suction source
20 tube
23 face of distal portion
23b face section opposite 23a
30 insulation covering 20
42 handle fitting
60 power supply

DETAILED DESCRIPTION OF THE INVENTION

The present invention is a monopolar suction coagulator. While the coagulator can be used for achieving hemostasis in any body part, it has particular utility in the nostril. The coagulator provides a more precise tip than known devices, is less prone to clogging, and is easier to unclog. It is simple to manufacture, rugged, and reliable.

Referring to FIG. 1, the coagulator (generally denoted 10) has a hollow elongate tube 20, insulation material 30 covering a major portion of the tube 20, a handle 40 of molding material covering a proximal section of the tube 20 and insulation material 30, a power cord 50 electrically connected to the tube 20, and a contact pin 52 terminating the power cord 50 for attachment to a power supply 60 capable of supplying coagulating current to the tube 20. The tube 20, insulation 30, and handle 40 are coaxial; the handle 40 extends furthest proximally and terminates in a fitting 42 that is engageable with an external suction source 70. As used herein, the distal direction is towards (and beyond) the coagulator 10 end that is inserted within a nostril (or other operative site), and the proximal direction is towards (and beyond) the coagulator 10 end that is handled by the physician or other operator.

Beveled Tip

Figure 2:
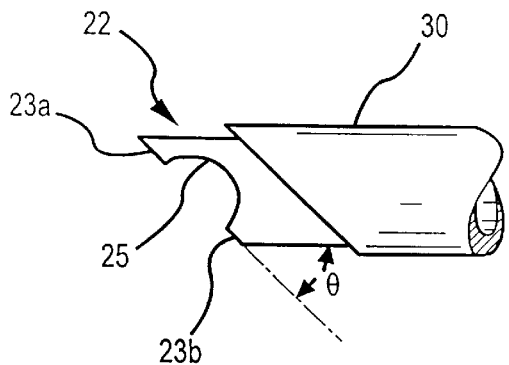
FIG. 2 is a detailed view of the tip portion of the coagulator of FIG. 1.

The tube 20 has a distal portion 22 that is uncovered by insulating material 30. When electrically activated, the distal portion 22 may be contacted with bleeding tissue to cauterize and coagulate the tissue and achieve hemostasis. The distal portion is shown in detail in FIG. 2, where it can be seen that it is beveled with respect to the tube 20 axis. The distal face (generally denoted 23, and further as 23a and 23b explained below) of the tube 20 occupies a plane forming an angle theta with respect to the tube 20 axis. As shown in FIG. 2, and presently preferred, the angle theta is 45 degrees. However, a useful device may have another bevel angle, and the angle is not critical to the invention. Because of the bevel, the distal face 23 has a section 23a that extends distal relative to an opposite section 23b. This distal face section 23a is in effect pointed, as can be perceived in FIG. 2 and is readily understandable. The greater the angle theta, the "sharper" the point formed at distal face section 23a. Stated another way, the greater the angle theta, the less material remains adjacent to distal face section 23a.

Figure 3:
FIG. 3 is a side elevation view of a prior art coagulator.

The distal section 23a allows for more precise coagulating than would an unbeveled tip (shown in FIG. 3 as prior art), because the sharpness of the distal face section 23a allows for better resolution than a comparatively blunt tip as in FIG. 3.

The bevel provides an additional advantage that is particularly useful for nasal coagulation. The distal face 23 is angled (at angle theta) with respect to the tube 20 axis. Coagulation occurs primarily by contacting the face 23 (and more particularly the distal face section 23a) with a side of a passageway, and it is easier to place the angled face onto a side of a nostril than is an unbeveled device. This is because the distal face section 23 "looks" to the side of the coagulator 10 (again at angle theta), whereas a face of an unbeveled instrument looks directly ahead (distal) to the instrument. The bevel allows the coagulator 10 to be inserted a distance along a linear passageway such as a nostril and then for the face 23 to be contacted to a portion of the passageway. Only the side of an unbeveled tube can be contacted against a nostril, instead of the more electrically active face. Stated another way, the bevel angle allows the coagulator 10 to tangentially coagulate with respect to the tube 20 axis.

Notch

Another feature of the coagulator 10 is the inclusion of notch 25 in the distal portion 22. The notch 25 can be a hemispherical cut-out section of the tube, with the plane of the distal face 23 approximately forming a base of the hemispherical cut-out (i.e., a plane forming a bisection of an imaginary sphere). The precise shape of the notch is not critical, and other shapes may be expected to provide similar results.

The notch 25 provides at least two benefits. The first is that it makes the distal face section 23a form a "sharper" point. The notch 25 results from the removal of material from the distal end 22, so that the distal face section 23a is more pointed. The distal face section 23a may be more precisely positioned, so that only bleeding tissue is cauterized and non-bleeding tissue is unaffected. If desired, however, the physician can contact the entire distal portion 22 (including the distal section 23b as well as the pointed distal face section 23a) with tissue, such as to sweep a relatively large (compared to the size of the distal face 23) tissue area.

The second advantage of the notch 23 relates to clogging. Prior art devices are known to include ventilation holes at a proximal location, and may be operated by placing and removing a finger over such a hole. These ventilation holes allow an amount of air to be drawn through the device along with blood and other tissue and smoke; otherwise such devices are prone to clogging with blood. Finger operated ventilation holes are cumbersome because the physician cannot easily rotate the device beyond the rotational capability of the human wrist, or about 180 degrees, since further rotation would require the physician's finger to leave the hole. The notch 25 allows an infusion of air into the tube 20 and handle 40, and reduces clogging similarly to a proximal ventilation hole. The notch 25 does not require a physician's continued effort to accomplish its function. And, the device 10 can be continually rotated by the physician without regard to finger placement. While the notch 25 does not preclude the use of a separate proximal vent hold if desired, the notch 25 has been found to greatly reduce clogging without another vent hole.

The notch 25 also facilitates tube 20 cleaning if the tube 20 becomes clogged. The clog can generally be accessed through the notch 25, so that the tube 20 can be easily cleared by wiping the distal portion 22 with a cloth. Absent the notch 25, the interior of the tube 20 cannot be easily accessed and cleaning requires a firm plunger or other specialized instrument. The quick and easy cleaning of the coagulator 10 prevents unwelcome cleaning delays that may be otherwise be necessary during an operation, and generally facilitates maintenance and hygiene.

Operation

The coagulator 10 is useful for achieving hemostasis in a patient's nose, although the scope of the invention is not limited thereto. A patient plate (such as, for example, a "BOVIE" plate available from one well known supplier) is engaged with the patient and the device 10 is engaged with the power supply 60 and suction source 70. The distal portion 22 of the tube 20 is placed within the bleeding nostril or other site. The physician contacts part of the distal portion 22 with the bleeding tissue to coagulate the same and achieve hemostasis. For the most precise coagulation, only the distal face section 23a is contacted to the bleeding tissue. If a relatively larger area of tissue is bleeding, the entirety of the distal portion 22 can be contacted with the nostril. Should the tube 20 become clogged, it can generally be unclogged by wiping the distal portion 22 with a cloth. The application of the coagulator 10 to the nostril is continued until hemostasis is achieved.

Sample Construction

The coagulator 10 can be constructed of many materials and sizes as will be apparent to those skilled in the art. A presently preferred embodiment is constructed substantially as follows.

The tube 20 is type 3003 full hard aluminum, having a size of 8 French. Known coagulators are somewhat larger, generally being size 10 French. The smaller size of the present coagulator 10 facilitates positioning within the nostril way, and is an improvement over known coagulators which are not generally adapted to be used within a nose. The tube 20 has a wall thickness of 0.014 inches. The bevel angle is 45 degrees, and the notch 25 has a 0.05 inch radius. This distal portion 22 extends about 0.1 inch distal to the insulation 30.

The insulation 20 is standard in the field, and the handle 40 molding is a material such as polypropylene. The overall coagulator 10 length is about 9 inches, and the tube 20 (and insulator 30) extends about 5 inches distal to the handle 40.

None of the foregoing dimensions and materials are critical to the practice of the present invention, and it will be appreciated that the invention may be modified in structure without departing from the spirit and scope of the invention as a whole.

The described invention provides a coagulator that is more positionable than known devices, less prone to clogging and easier to unclog, while maintaining the essential simplicity and reliability of known coagulators.

What is claimed is:

1. An electrosurgical suction coagulator comprising:
   a hollow elongate electrically conductive tube having a proximal end and a distal end, said elonoate tube defining an axis therethrough;
   electrically insulating material covering a major portion of said tube, said material leaving a distal tube section uncovered;
   a handle covering a proximal section of said insulating material and said tube, said handle having a fitting for engagement with a suction source; and
   a power cord electrically engaged with said tube and with a power supply for supplying coagulating current to said tube;
   wherein the distal tube section is beveled at an angle with respect to the tube axis;
   wherein the distal tube section has a notch;
   wherein the notch is hemispherical.

2. The electrosurgical catheter of claim 1, wherein the hemispherical notch has a radius of about 0.05 inches.

3. The electrosurgical catheter of claim 2, wherein the hemispherical notch has a base that forms an angle with respect to the tube axis that is equal to the angle of the distal tube section bevel.

4. An electrosurgical suction coagulator comprising:
   a hollow elongate electrically conductive tube having a proximal end and a distal end, said elongate tube defining an axis therethrough;
   electrically insulating material covering a major portion of said tube, said material leaving a distal tube section uncovered;
   a handle covering a proximal section of said insulating material and said tube, said handle having a fitting for engagement with a suction source; and
   a power cord electrically engaged with said tube and with a power supply for supplying coagulating current to said tube;
   wherein the distal tube section has a notch;
   wherein the notch is hemispherical.

5. The electrosurgical coagulator of claim 4, wherein the hemispherical notch has a radius of about 0.15 inches.

6. The electrosurgical coagulator of claim 5, wherein the hemispherical notch has a base that forms an angle with respect to the tube axis that is equal to the angle of the distal tube section bevel.

7. An electrosurgical suction coagulator comprising:
   a hollow elongate electrically conductive tube having a proximal end and a distal end, said elongate tube defining an axis therethrough;
   electrically insulating material covering a major portion of said tube, said material leaving a distal tube section uncovered;
   a handle covering a proximal section of said insulating material and said tube, said handle having a fitting for engagement with a suction source; and
   a power cord electrically engaged with said tube and with a power supply for supplying coagulating current to said tube;
   wherein the distal tube section has a distal face; and
   wherein the distal tube section has a notch, the notch being a cut-out section extending proximally from the distal face.

8. The coagulator of claim 4, wherein the distal tube section is beveled.

* * * * *